United States Patent [19]

Matsui et al.

[11] Patent Number: 5,070,300
[45] Date of Patent: Dec. 3, 1991

[54] APPARATUS FOR MEASURING BREAKDOWN PLASMA

[75] Inventors: Tetsuya Matsui, Hitachi; Takehiko Kitamori, Ushiku; Kenji Yokose, Hitachi; Masaharu Sakagami, Katsuta, all of Japan

[73] Assignee: Hitachi, Ltd., Tokyo, Japan

[21] Appl. No.: 390,762

[22] Filed: Aug. 8, 1989

[30] Foreign Application Priority Data

Aug. 18, 1988 [JP] Japan .................. 63-205391

[51] Int. Cl.[5] .......................... G01N 27/62
[52] U.S. Cl. .................. 324/464; 324/71.4; 356/336
[58] Field of Search ............ 356/336, 432; 324/71.4, 324/464, 459

[56] References Cited

U.S. PATENT DOCUMENTS

| | | | |
|---|---|---|---|
| 3,519,927 | 7/1970 | Holt | 324/71.4 |
| 3,853,750 | 12/1974 | Volsy | 324/71.4 |
| 3,953,792 | 4/1976 | Fletcher | 324/71.4 |
| 4,662,749 | 5/1987 | Hatton et al. | 356/336 |
| 4,722,602 | 2/1988 | Kitamori et al. | 356/336 |
| 4,767,591 | 8/1988 | Wampler | 324/71.4 |

FOREIGN PATENT DOCUMENTS 550560 12/1975 U.S.S.R. .................. 324/464
548145 3/1980 U.S.S.R. .................. 324/464

OTHER PUBLICATIONS

Tellus (Journal of Geo Physics), 1966 pp. 573–586 Electric Aerosol Particle Counting and Size Distribution Measuring, Whitby et al.

*Primary Examiner*—Kenneth A. Wieder
*Assistant Examiner*—Maura K. Regan
*Attorney, Agent, or Firm*—Antonelli, Terry, Stout & Kraus

[57] ABSTRACT

Apparatus for measuring breakdown plasma, comprising an irradiating device for irradiating a sample with a focused light beam and for causing breakdown of a ultrafine particle to be measured in the sample at the focused beam region to change the particle into plasma; a pair of electrodes arranged on opposite sides of the focused region of the beam; and a device for measuring an electrical resistance between the electrodes under a condition where the breakdown plasma is produced between the electrodes and for determining a diameter of the particle according to the measured electrical resistance serves for accurate measurement of the diameter of the ultrafine particle in the sample.

8 Claims, 7 Drawing Sheets

APPARATUS FOR MEASURING BREAKDOWN PLASMA

FIELD OF INVENTION

The present invention is concerned with an apparatus for detecting particulate materials or particles in a liquid or gaseous sample, and more specifically is concerned with an analyzing apparatus for counting the number of the particles in the sample and for measuring diameters of the particles.

DESCRIPTION OF RELATED ARTS

It has already been proposed to cause a breakdown of the particles in a liquid sample to produce breakdown plasma by irradiating the sample with a light beam focused to have a high energy density, for the breakdown and to detect the acoustic signal produced upon the electric breakdown, so as to count the number of the particulate materials or ultrafine particles in the liquid sample, in T. Kitamori et al, "Laser Breakdown Acoustic Effect of Ultrafine Particle in Liquids and Its Application to Particle Counting" Jap. J. of Appl. Phys. 27 (1988) L983-L985, and T. Kitamori et al, "Detection of Ultrafine Particles in Liquids Using a Breakdown Acoustic Effect" Opt. Sci. 58 (1988) 150-151. In addition, it is also disclosed in Kitamori et al's prior application (Japanese Patent Application No. 63-85094 corresponding to U.S. Ser. No. 334,358 filed on Apr. 7, 1989 and European Pat. Appln. No. 89106142.6) to count the number of particles not only in the liquid sample but also in the gaseous sample, and to measure the diameter of the particle utilizing the breakdown plasma above.

The term "breakdown plasma" is referred herein to a plasma produced from a particle in a very short time after the irradiation of the high energy density light beam such as focused high energy laser beam having an energy density or equivalently an intensity of an electric field not lower than a certain critical or threshold energy density or electric field intensity proper to composition and crystalline state etc. of each particle, which has been explained in detail in the prior application and Kitamori et al's literature above.

In the meantime, as disclosed in the Kitamori et al's prior patent application, the analysis of particles in the fluid described in the Kitamori et al U.S. Pat. No. 4,722,602 included the analysis of the breakdown plasma.

All the conventionally proposed methods for analyzing the sample above were directed to detecting an optical or acoustic signal produced upon the breakdown of the particle in the sample so as to count the number of the particles in the sample and to measure the diameters thereof. These conventional or prior arts provide an accurate method and apparatus for counting the number of the particulate materials.

In detecting the optical or acoustic signals as in the above-mentioned conventional technique, however, the diameters of the particles can not be measured very accurately, because the diameter of the breakdown plasma produced by the breakdown of the particle and dependent on the diameter of the particle subjected to the breakdown becomes greater than the width or diameter of the irradiated light beam, while the intensity of the optical or acoustic signal depends on the area of the plasma region where the light beam is irradiated.

SUMMARY OF INVENTION

The present invention has been made to solve the problem above and the first object of the invention is to provide an apparatus for measuring breakdown plasma capable of measuring the diameter of the breakdown plasma accurately and therefore the diameter of the particle accurately.

A second object of the invention is to provide an apparatus for measuring the breakdown plasma capable of detecting the number of occurences of breakdown plasma and detecting the diameters thereof and therefore counting/measuring the number (and hence concentration or density) of particles/diameter thereof.

A third object of the invention is to provide a new type of apparatus for measuring the number of the breakdown plasma.

The first object can be attained, in accordance with the invention, by a breakdown plasma measuring apparatus having means for detecting a change in an electrical resistance between a pair of electrodes under a condition where the breakdown plasma is produced therebetween due to the breakdown of the particle by the irradiation of the focused light beam to the particle in the sample, and for determining a diameter according to the measured resistance. The resistance can be equivalently substituted by a conductance or an average conductivity between the electrodes.

The second or third object above is attained by the provision of means for determining the number of the particles to be measured from the number of changes in the electrical resistance between the pair of electrodes due to the corresponding number of occurrences of the breakdown plasma.

More specifically and preferably, the light beam from a light source is focused by a lens system to irradiate the sample. The intensity of the light beam is selected such that the energy density of the light beam exceeds the breakdown threshold of the particle to be measured in the focused region. A voltage is applied across a pair of electrodes arranged to be faced to each other on opposite sides of the region where the breakdown is generated. The voltage may be d.c. or a.c. The area of each electrode is preferably greater than a sectional area of the region where the breakdown may occur. In other words, the focused beam region where the breakdown may occur is preferably restricted within a region between the planes of the electrodes. The electrical conductance of the region between the electrodes is increased (i.e. the resistance therebetween is decreased) and therefore the electric current between the electrodes is increased. The number of increases is counted to determine the number of the particles in the sample and the magnitude of the increased current is detected to determine the diameter of the particle. The presense of the air or other gas bubbles will not increase but decrease the conductance and therefore will not affect the counting of the number of the particles or the measurement of the diameter.

BRIEF DESCRIPTION OF THE DRAWINGS

The above-mentioned and other objects as well as the above-mentioned and other features of the invention will be made clearer from the description of preferred embodiments of the invention referring to the accompanied drawings in which.

DETAILED DESCRIPTION OF PREFERRED EMBODIMENTS

Figure 1:
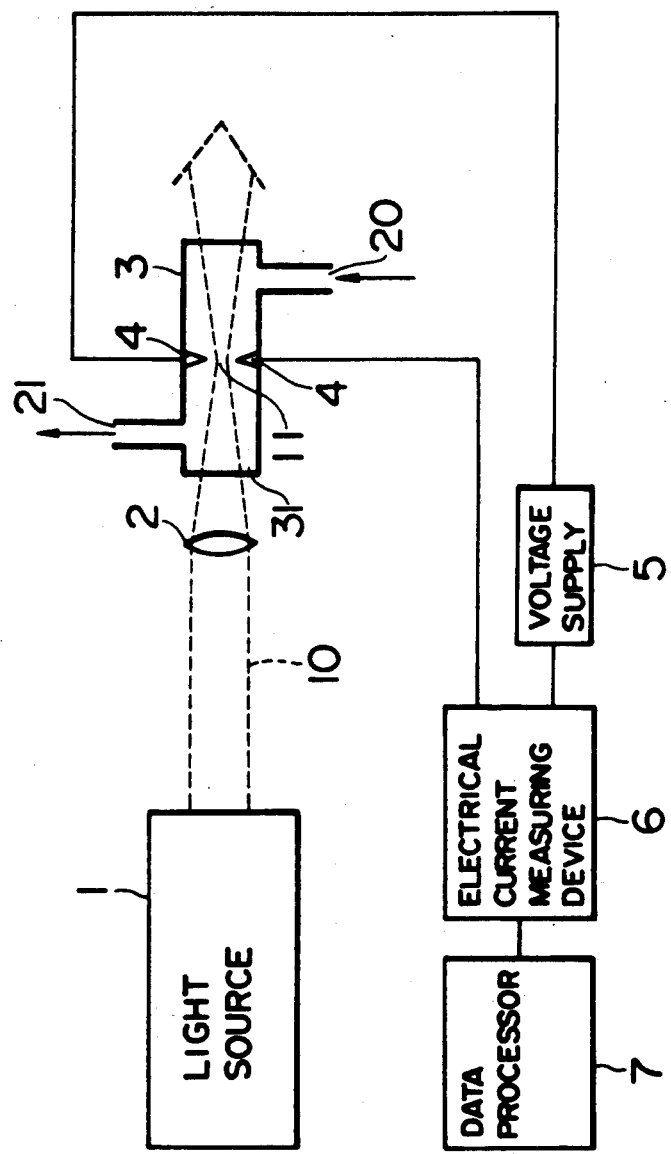
FIG. 1 is a schematic view of an apparatus according to a preferred embodiment of the invention.

An embodiment of the invention is explained referring to FIG. 1. At first, outline of the construction of the embodiment is explained.

The fluid sample is flown from an inlet 20 to an outlet 21 through a region between a pair of electrodes 4,4 in a cell 3. Light beam for excitation from a light source 1 is focused by a lens system 2 to form a high energy density region 11, which is referred to hereinafter as "beam waist region". The breakdown of a particulate material or particle to be measured in the sample flowing through the cell 3 is caused in the beam waist region 11 and the breakdown plasma is produced. The pair of electrodes 4,4 are disposed on both or opposite sides of the beam waist region 11. A voltage is applied from a voltage supply 5 across the electrodes 4,4 and an electric current passing through the electrodes 4,4 is measured by an electrical current measuring device 6. When the breakdown plasma is generated, a conductance and therefore an average conductivity of a region between the electrodes 4,4 are increased (i.e. electrical resistance is decreased) and the magnitude of the electric current is also increased. Information of a number of increases in the current and the magnitude of the current is stored in a data processor 7 and then the number of the particles and the diameters of the particles are determined from the stored information. The magnitude of the current is preferably a peak current or other quantity equivalent thereto.

The main construction of the apparatus is further explained. The source may comprise a high power laser, because the source 1 is required to provide an energy high enough to cause the breakdown of the particle. The volume of the beam waist region 11 becomes smaller as the focal length of the lens 2 becomes shorter. Thus, the focal length of the lens 2 is appropriately selected according to a concentration of the particles to be measured in the sample. The beam waist region 11 is explained more in detail in the Kitamori et al's JJAP literature mentioned above. As to materials of the cell 3, optical window part 31 from which excitation beam 10 enters the cell 3 is made for example from quartz glass having high transmittance or low absorption of the excitation light beam 10. The electrodes 4,4 are made from metallic material which can endure the shock wave upon the breakdown. The electrodes 4,4 are securely supported so that the distance therebetween is not changed. The electrodes 4,4 may be supported in such a manner that the distance therebetween is adjustable as explained later in detail referring to FIG. 7. The voltage supply 5 is preferred to have high stability so that the measurement accuracy is enhanced and ensured. The current measuring device 6 is preferred to respond very rapidly. When the source 1 comprises a pulse laser, the width of the laser pulse is in the order of $10^{-3} - 10^1$ nsec and the lifetime of the breakdown plasma produced thereby is thought to be in the order of $10^1-10^3$ μsec. Thus, the current measuring device 6 should respond rapidly enough to measure the change in the conductance or resistance due to the production and presence of the breakdown plasma.

Now, principle of the embodiment of FIG. 1 is explained.

Figure 2:
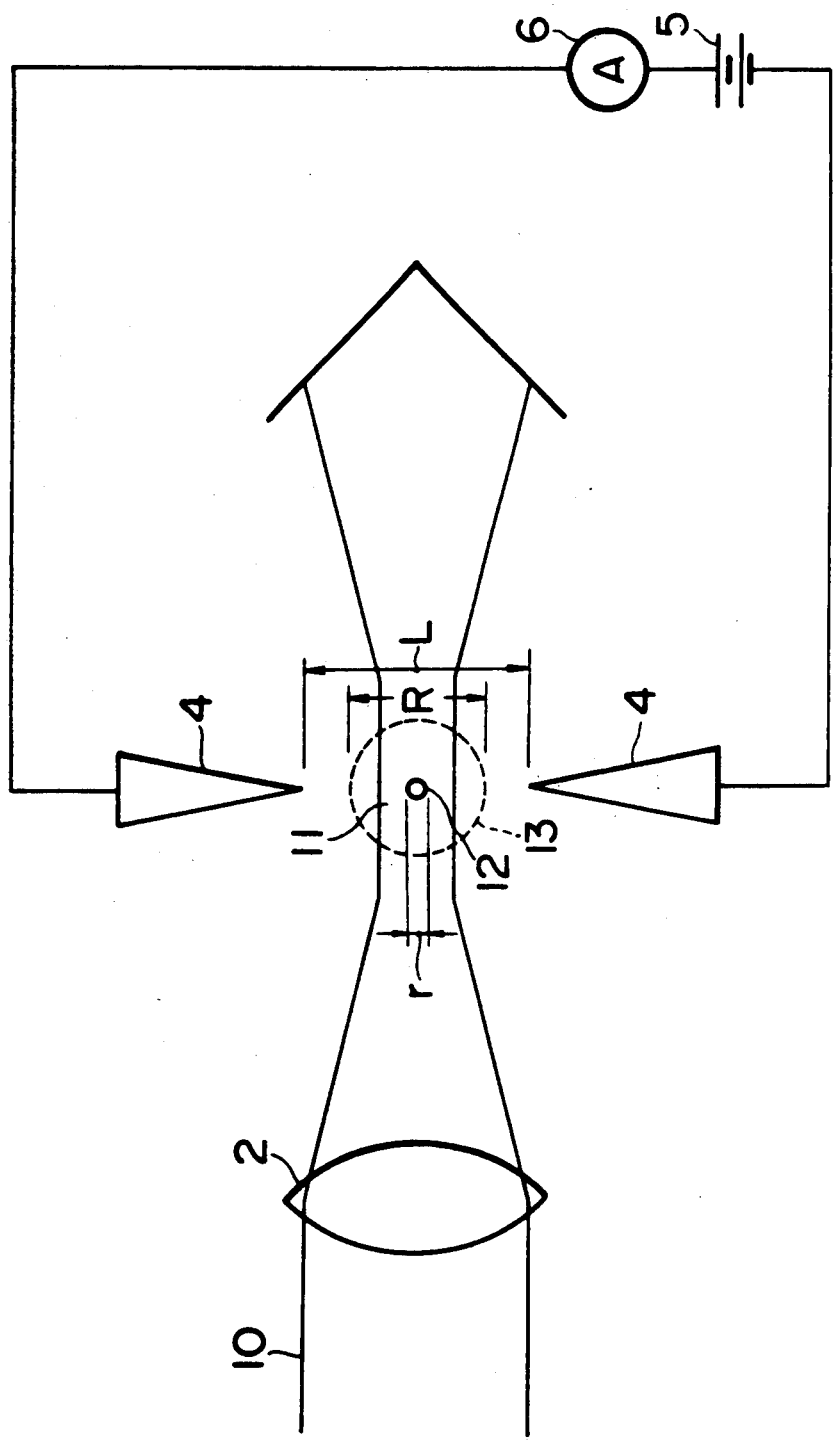
FIG. 2 is a drawing illustrating a measurement principle of the invention.

FIG. 2 shows a part for detecting the breakdown plasma in an enlarged form. The electric field intensity or energy density of the excitation light beam 10 in the beam waist region 11 is selected to be higher than the breakdown threshold of the particles 12 to be measured in the sample, while it is selected to be lower than a breakdown threshold of the sample medium around the particles 12. The breakdown threshold energy density is, for example, in the order of $5 \times 10^{12}$ W/cm$^2$ in gaseous phase, $3 \times 10^{11}$ W/cm$^2$ in case of water, and $10^{10}$ W/cm$^2$ in case of solid phase. Therefore, when the energy density of the light beam at the beam waist region 11 is selected to be higher than $10^{10}$ W/cm$^2$ and lower than $3 \times 10^{11}$ W/cm$^2$, only the solid matter or particles in the water or gas can be subject to the breakdown. The breakdown threshold is varied depending on the kinds of solid material. However, the range of variation lies in a region between $10^{10}$ W/cm$^2$ and $3 \times 10^{11}$ W/cm$^2$. Thus, almost all the solid material or particles 12 can be broken down under the high electric field of the light beam when the energy density at the beam waist region 11 is selected to be in the order of $10^{11}$ W/cm$^2$.

Every time when a particle 12 in the sample enters the beam waist region 11, the breakdown plasma 13 is produced. The electrical conductivity of each of the breakdown plasma and the sample media is shown in the Table 1 below.

TABLE 1

| Material | Comparison Of Conductivity Conductivity (ohm$^{-1}$ · cm$^{-1}$) |
|---|---|
| Breakdown plasma | $10^1-10^2$ |
| Purified Water | $10^{-8}$ |
| Polystyrene | $10^{-16}$ |
| Gas | less than $10^{-16}$ |

Figure 3:
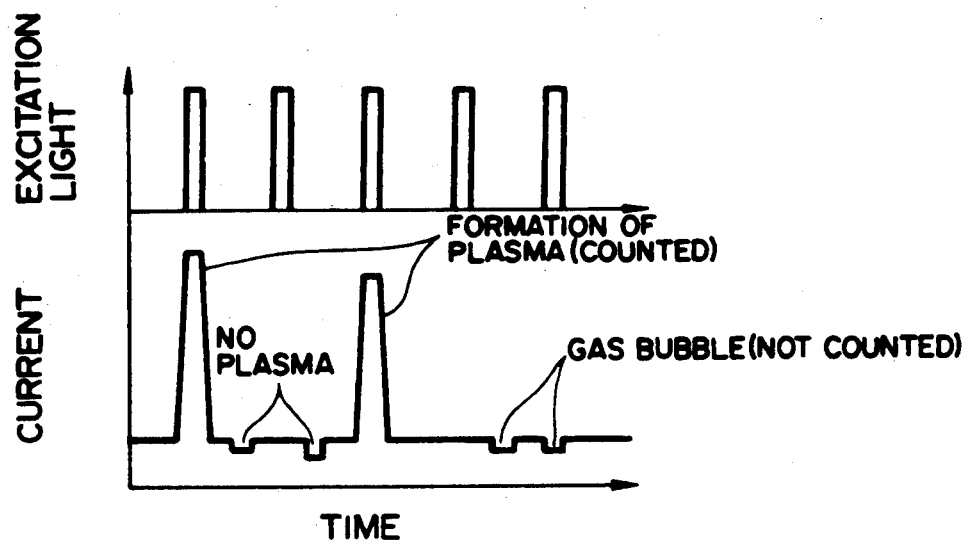
FIG. 3 is a time chart of excitation light beam to be irradiated and an electrical current to be measured.

The electric current between the electrodes 4,4 is increased when the breakdown plasma 13 is produced, because the conductivity of the breakdown plasma 13 is much higher than that in the other states, which may be present, as seen from Table 1. The change in the electrical current is shown in FIG. 3. When the excitation light beam 10 is irradiated in the form of pulses, the electric current between the electrodes 4,4 is increased, if the particle 12 is present in the beam waist region 11 at a time when the excitation pulse 10 is irradiated. On the other hand, the current is not changed significantly, even if the particle 12 passes through the region between the electrodes 4,4, when the excitation light pulse 10 is not irradiated.

An expected value at which the particle 12 is present in the beam waist region 11 upon irradiation of the excitation pulse 10 depends on a product between a volume V of the beam waist region 11 and number concentration N of the particles 12 in the sample. The probability at which more than two particles are present in the beam waist region 11 at the same time, i.e. during a time period when one excitation pulse is irradiated, is assumed to be substantially negligible. It is also assumed that the breakdown plasma is produced in such a manner that substantially the whole part of the particle 12 is changed into the plasma every time when the particle 12 is irradiated at a time when the particle 12 is present in the beam waist region 11. In this case, a count C defined by number of occurrences of the current change for n excitation pulses can be expressed as C=nVN. As V and n can be known beforehand in the actual measurement, the number density or concentration N of the particles 12 can be determined, if the count C is measured. When the liquid sample is measured, the air or other gas bubbles do not substantially affect the electric current because the breakdown of the bubble is not caused, even when the bubble is present in the beam waist region 11. Thus, when the number of occurrences of the current increase C under the given number of shots n, i.e. number of excitation pulses n is counted, the number of the particles 12 can be determined.

In FIG. 2, assuming the plasma density in the breakdown plasma 13 is constant, the diameter R of the breakdown plasma 13 can be expressed as $$R = c.r \qquad (1),$$

where "r" is a diameter of the particle 12 to be measured, and "c" is a constant dependent on the intensity or energy density of the light beam at the beam waist region 11 and kinds of the material of the particle 12 etc.

Figure 4A:
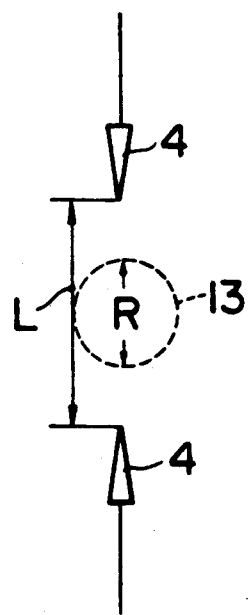
FIG. 4A and 4B are schematic illustrations of one-dimensional and two-dimensional measurements respectively.

At first, a one-dimensional approximation or model as shown in FIG. 4A is considered where the electric current is assumed to flow in a plane of the sheet of the drawing in the direction of the electric field between the pointed electrodes 4,4 perpendicular to the optical axis. As the electrical resistance between the electrodes 4,4 linearly depends on the length of the plasma region and the sample medium region, an electric current I between the electrodes 4,4 can be expressed as $$I = V/[a.(L-R) + b.R] \qquad (2),$$

where "V" is a voltage between the electrodes 4,4, "L" is a distance between the electrodes 4,4, and "a" and "b" respectively represent resistivities per unit length of the sample medium and plasma.

In a case where the breakdown plasma is present in a purified water, "a" and "b" will be $10^8$ Ω.cm and $10^{-1}$–$10^{-2}$ Ω.cm respectively. When b=$10^{-2}$ Ω.cm, L=500 μm, and V=1000 volts, the relationship between R and I can be plotted as the curve in FIG. 4C. FIG. 4C clearly shows that the electric current I is increased according to the increase in the diameter R of the breakdown plasma. The magnitude of the electric current I is in the order of milli-ampere, and can be measured accurately. The magnitude of the current will, however, be changed when the center of the plasma is not situated on a line connecting pointed electrodes 4,4.

Figure 4B:
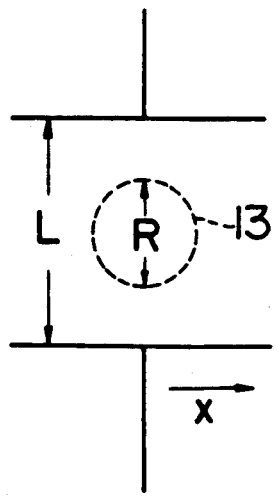
Figure 4C:
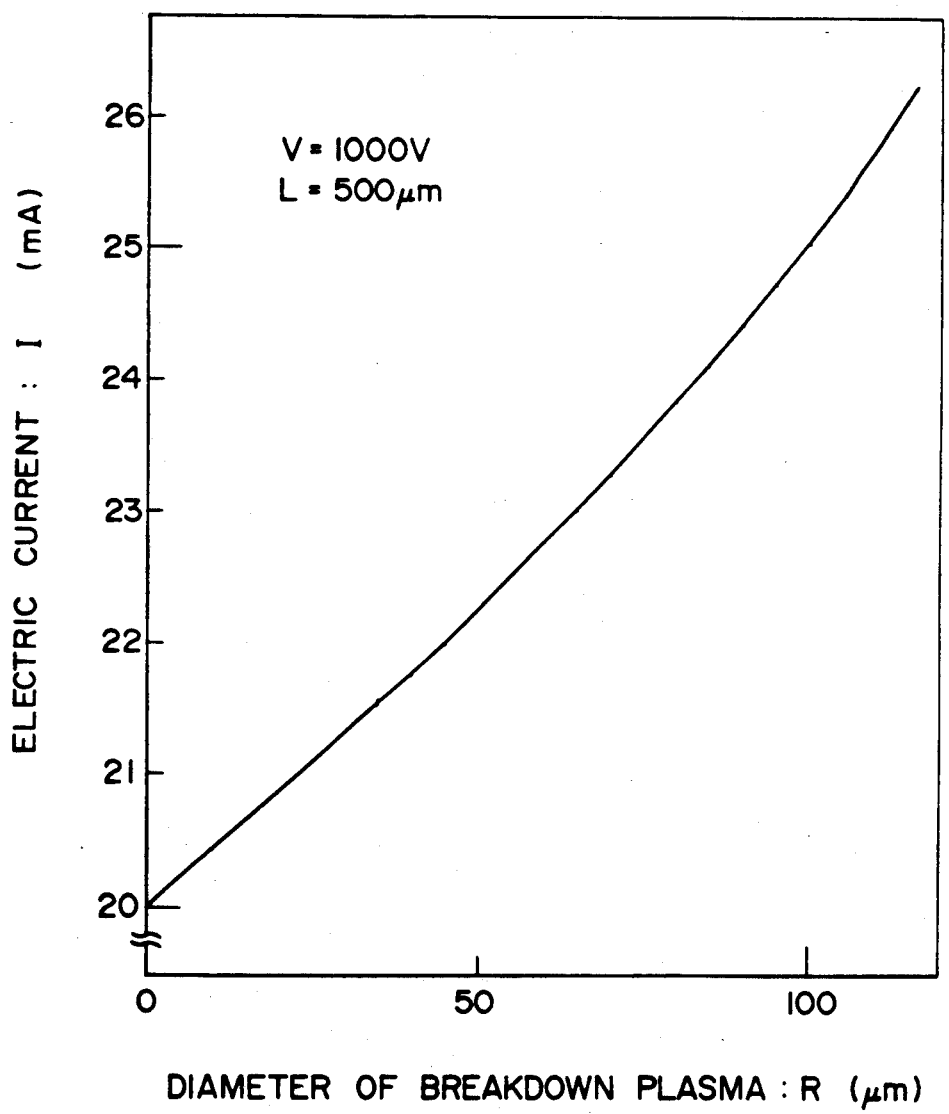
FIG. 4C shows a relationship between an electric current I and a diameter of breakdown plasma in an example of one-dimensional model.

In a two dimensional approximation or model as shown in FIG. 4B where the electric current is assumed to flow in a plane of the sheet of the drawing extended in the direction "X" of the optical axis of the excitation beam and in the direction of the electric field between two planar electrodes 4,4, the change in the electric current will be relatively or negligibly small even when the position of the plasma 13 is changed in the direction "X".

It will be qualitatively apparent that the current I is increased according to the increase in the diameter of the breakdown plasma 13 in the two-dimensional model as in the one-dimensional model, if the first order approximation is taken.

The diameter r of the particle to be measured can be determined by measuring the current I or equivalently electrical resistance, because the diameter R of the breakdown plasma depends on the diameter of the particle to be measured as shown in equation (1). Ultrafine particles having diameter of r≈$10^{-2}$ μm or more can be changed into the breakdown plasma. The diameter r can be determined from the electric current I or corresponding electrical resistance if the breakdown plasma can be produced. So long as the particle can be changed into breakdown plasma, the diameter r can be measured, even if the diameter r is less than $10^{-2}$ μm.

When the particle having a diameter of approximately r≈$10^{-2}$ μm is subject to breakdown, the diameter R of the thus formed breakdown plasma is in the order of $10^0$–$10^1$ μm. The distance L between the electrodes 4,4 should be greater than the diameter R of the plasma to measure the current. The distance L is, however, preferred to be as small as possible to derive a signal having a high signal-to-noise ratio, so long as the condition L>R is satisfied.

As explained above, the number and hence concentration or density of the particles to be measured as well as the diameter thereof can be measured according to the embodiment above.

Figure 5A:
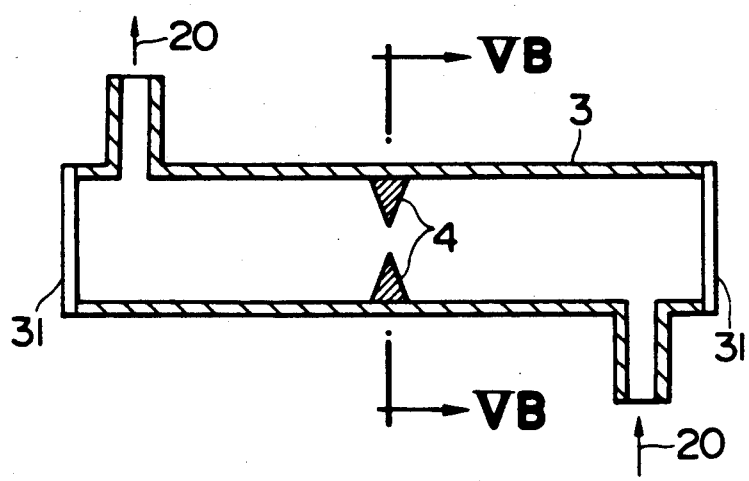
FIG. 5A is a vertical sectional view of an embodiment of a measurement cell used in the apparatus of the invention.
Figure 5B:
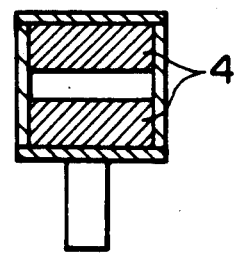
FIG. 5B is a sectional view of the cell of FIG. 5A along a line VB—VB.

FIGS. 5A and 5B show a preferred embodiment of the configuration of the cell 3 and the electrodes 4,4 therein. In the cell 3 of FIGS. 5A and 5B, excitation light beam 10 which has passed through the optical window 31 is focused to form the beam waist region at a position between the electrodes 4,4. The sample is introduced from the inlet 20, passed through the region between the electrodes 4,4, and then flown out of the outlet 21. As the region between the electrodes 4,4 is much narrower than the other passage of the sample in the cell 3, the passage between the electrodes 4,4 are preferably arranged uniformly narrow along the width thereof as seen from the FIG. 5B so as to avoid the sample to be stagnated at a local area around the electrodes 4,4. Thus, the inaccurate measurement due to the stagnation of the sample around the electrodes 4,4 can be avoided.

Figure 6A:
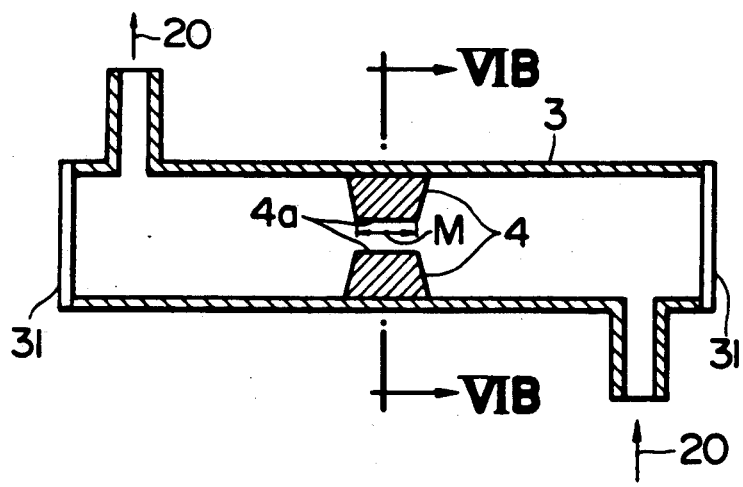
FIG. 6A is a vertical sectional view of another embodiment of a measurement cell used in the apparatus of the invention.
Figure 6B:
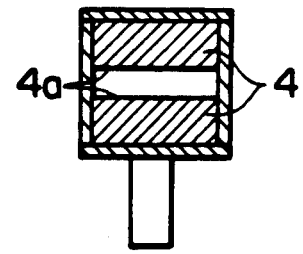
FIG. 6B is a sectional view of the cell of FIG. 6A along a line VIB—VIB.

FIGS. 6A and 6B shows another preferred embodiment of the invention, where the distal end of each electrode 4 is in the form of a plane 4a. The electrodes 4,4, are arranged so that the planes 4a,4a are parallel to the direction of the excitation beam 10 and the flow of the sample in the cell 3. As the beam waist region is generally cylindrical having an axis parallel to the advancing direction of the excitation beam 10, the breakdown plasma can be accurately measured without being affected by the position of the generation of the breakdown plasma in the advancing direction of the beam 10, although the breakdown may be caused at any position within the beam waist region. In this case the length M of the electrode planes 4a,4a in the light advancing direction is preferably selected to be longer than the length of the beam waist region.

Figure 7:
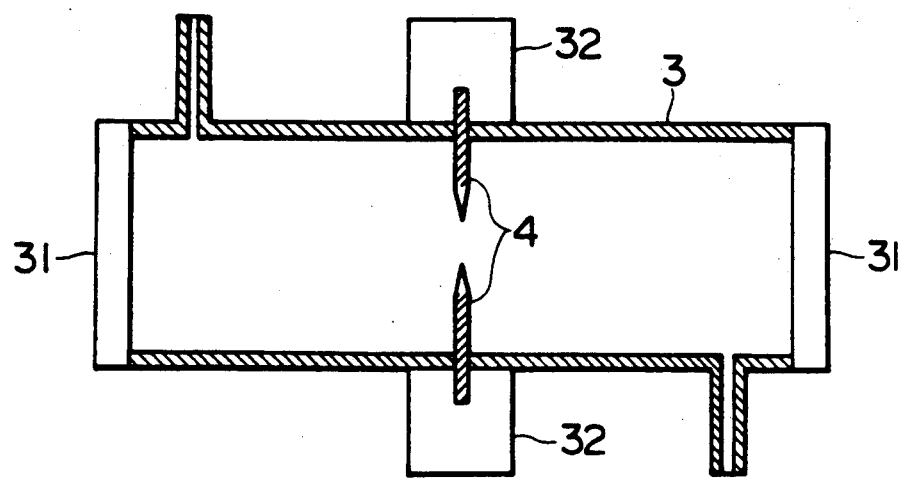
FIG. 7 is a vertical sectional view of still another embodiment of a measurement cell used in the apparatus of the invention where the distance between the electrodes is variable.

A still another embodiment of the cell in the apparatus according to the invention is shown in FIG. 7. In this embodiment, an electrode position control devices 32,32 are provided on the cell 3 for controlling the positions of electrodes 4,4. As apparent from simple geometrical consideration or equation (2), the measured current I depends not only on the diameter R of the breakdown plasma but also on the distance L between the electrodes 4,4. As the distance L approaches the diameter R, the current I increases. In this embodiment, optimum measurement condition can be established by adjusting the distance L between the electrodes 4,4.

Each of the cells 3 in the above-mentioned embodiments can for example be used for measuring the concentration or density of a very small amount of impurity particles contained in process fluid for manufacturing a semiconductor or a semiconductor device and/or for measuring diameters thereof, when the process fluid is passed through the cell 3 as the sample.

Figure 8:
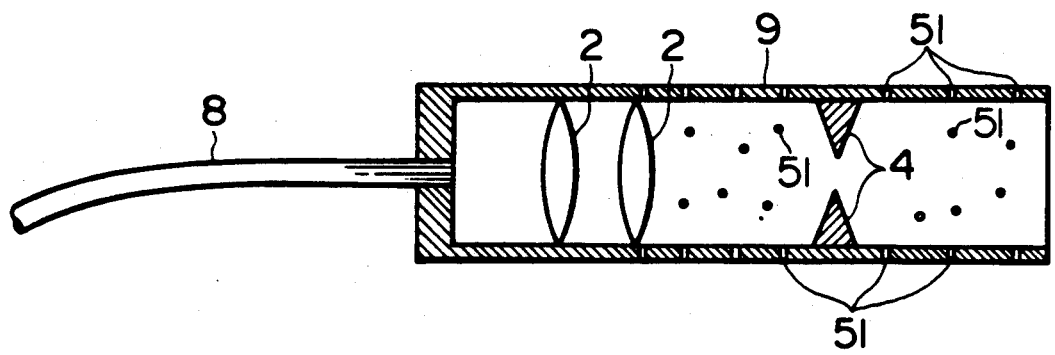
FIG. 8 is a still another embodiment of the measurement cell in the form of a probe.
Figure 9:
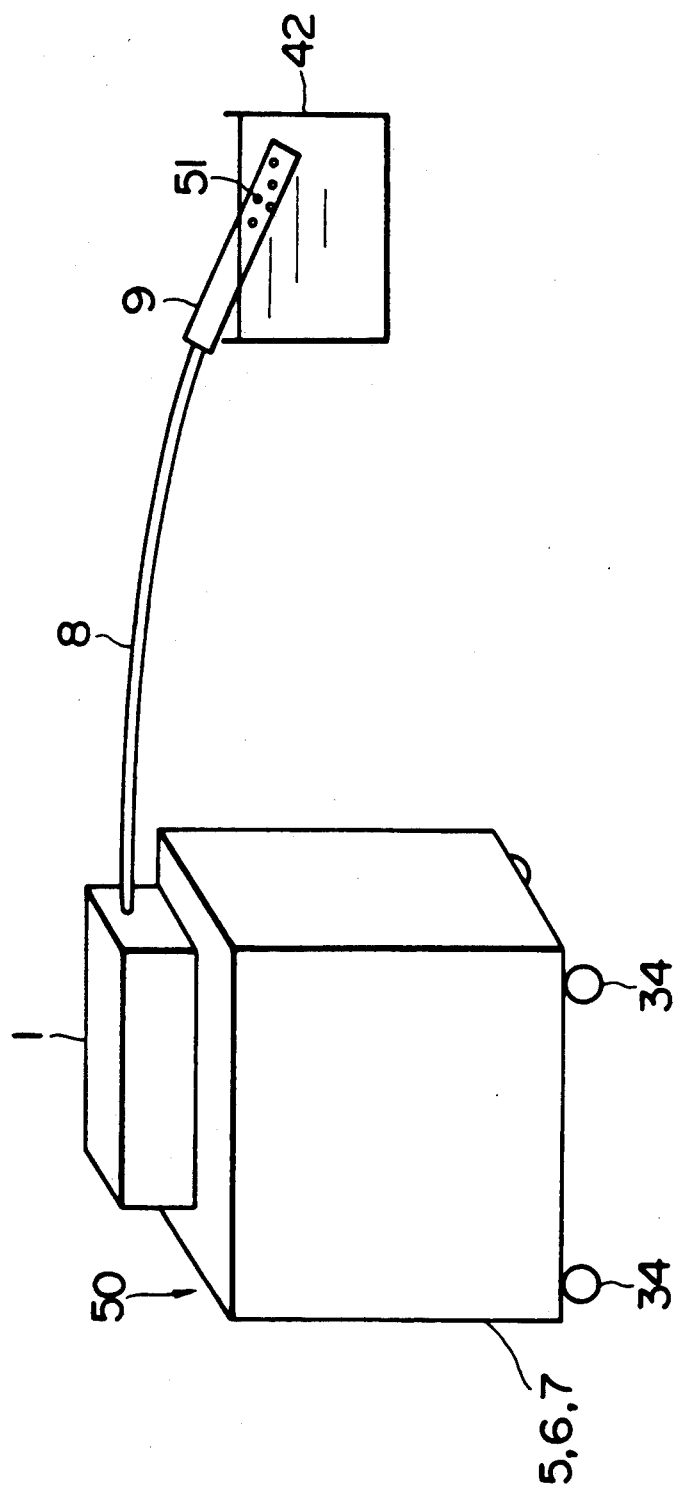
FIG. 9 is an explanatory view of the apparatus according to another embodiment of the invention having the probe of FIG. 8.

FIGS. 8 and 9 show a still another embodiment of the invention is which a probe 9 is connected to an optical fiber 8. The probe 9 is immersed into a bath 42 where sample or liquid to be measured is filled. More specifically, a housing 50 having elements shown in FIG. 1 such as the light source 1, the voltage supply 5, the current measuring device 6 and data processor 7 incorporated therein is movably carried by casters 34. In this embodiment, a part for detecting the breakdown plasma is arranged in the form of the probe 9 utilizing the optical fiber 8. The excitation light beam 10 from the source 1 through the optical fiber 8 is focused by the lens system 2 in the probe 9 attached at the exit end of the optical fiber 8. The breakdown plasma generated by the focused beam is detected by the electrodes 4,4 in the manner explained before. The source and the current measuring system are the same as those explained before. Reference numeral 51 denotes a penetrating hole. This embodiment is advantageous because the detection part can be moved easily and freely to a position where the measurement is to be made.

As explained, the invention is advantageous because the number and diameters of the breakdown plasma can be accurately measured and therefore the number (and hence concentration or density) and diameters of the particles in the sample can be accurately measured.

What is claimed is:

1. An apparatus for measuring characteristics of breakdown plasma, said apparatus comprising:
    irradiating means for irradiating a sample with a focused light beam and for causing breakdown of a particle to be measured in the sample at a focused beam region to change the particle into plasma;
    a pair of electrodes arranged on opposite sides of the focused beam region; and
    means for measuring an electrical resistance between the electrodes under a condition where the breakdown plasma is produced between the electrodes and for determining a diameter of the particle according to the measured electrical resistance.

2. An apparatus according to claim 1, wherein an energy density of the light beam at the focused beam region is higher than a breakdown threshold of the particle to be measured in the sample and is lower than a breakdown threshold of the sample medium around the particle.

3. An apparatus according to claim 1, further comprising means for detecting a change in the electrical resistance between the electrodes due to the production of the breakdown plasma, for counting a number of changes in the electrical resistance, and for determining a number of particles in the sample according to the counted number of changes.

4. An apparatus according to claim 1, wherein the electrodes extend transversely with respect to a direction along which the sample is flown so that a distance between the electrodes is uniform.

5. An apparatus according to claim 4, wherein opposed end faces of the electrodes are made in the form of planes parallel to an advancing direction of the light beam.

6. An apparatus according to claim 5, wherein the focused beam region is restricted within a region between the planes of the electrodes.

7. An apparatus according to claim 1, further comprising means for adjusting a distance between the electrodes.

8. An apparatus according to claim 1, further comprising:
    an optical fiber for transmitting the light beam from a light beam source to the sample; and
    a probe connected to an exit end of the optical fiber and incorporating therein a lens system for focusing the light beam from the exit end of the optical fiber and the pair of electrodes on the opposite sides of the focused beam region.

* * * * *